United States Patent [19]

Anderson, deceased et al.

[11] Patent Number: Plant 5,478

[45] Date of Patent: May 28, 1985

[54] CHERRY TREE (KING-44-P-477)

[76] Inventors: Fred W. Anderson, deceased, late of Merced, Calif.; by Wendel J. Olson, heir, 6015 N. Country Club Pl., Merced, Calif. 95340

[21] Appl. No.: 528,900

[22] Filed: Sep. 2, 1983

[51] Int. Cl.[3] ..... A01H 5/03

[52] U.S. Cl. ..... Plt./37

[58] Field of Search ..... Plt./37

*Primary Examiner*—Robert E. Bagwill

*Attorney, Agent, or Firm*—Roger B. Webster

[57] ABSTRACT

A cherry tree which is large, vigorous, upright, dense, vase-formed, and hardy; foliated with large, ovate, medium thick, smooth, abruptly pointed, dark green leaves having a crenate to coarsely serrate margin, a petiole of medium length and thickness, and medium size, alternate, reniform, red glands; blooms early from hardy, free buds of medium size and length; the flowers being of medium size and white; and is a regular and very productive bearer of early and evenly ripening, semi-freestone, uniform, medium size fruit broadly compressed toward the suture, the fruit having thick to medium thick, tough skin dark purple when eating ripe, and red flesh.

1 Drawing Figure

BACKGROUND OF THE VARIETY

1. Field of the Invention:

Over a substantial number of years, and in an extensive plant breeding program conducted at his experimental nursery and orchard located near Le Grand, Merced County, Calif., Frederic W. Anderson, now deceased, originated a large number of new and distinct varieties of fruit trees, and which included the hereinclaimed variety of cherry tree.

2. Classification of the Variety:

The present variety of cherry tree is embraced by Class 37, Plants, of the United States Patent Office Manual of Classification.

3. Prior Varieties:

Among the existent varieties of cherry trees which were known to originator, particular reference is made to Bing (unpatented) and Bing d'Andy (U.S. Plant Pat. No. 2,198).

ORIGIN OF THE VARIETY

The present variety of cherry tree was originated in the aforesaid experimental nursery and orchard as a seedling produced from an open-pollinated Bing d'Andy seed.

ASEXUAL REPRODUCTION OF THE VARIETY

Subsequent to origination of the present variety of cherry tree, it was asexually reproduced—by originator—by grafting and budding on suitable rootstock, and in maturity such reproductions ran true to the original tree in all respects.

SUMMARY OF THE VARIETY

The present variety of cherry tree is, characteristically, large, vigorous, upright, dense, vase-formed, and hardy; foliated with large, ovate, medium thick, smooth, abruptly pointed, dark green leaves having a crenate to coarsely serrate margin, a petiole of medium length and thickness, and medium size, alternate, reniform, red glands; blooms early from hardy, free buds of medium size and length; the flowers being of medium size and white; and is a regular and very productive bearer of early and evenly ripening, semi-freestone, uniform, medium size fruit broadly compressed toward the suture, the fruit having thick to medium thick, tough skin dark purple when eating ripe, and red flesh.

The present variety of cherry tree is further characterized by flowers which bloom approximately four days before the Bing, and by fruit which ripens approximately one week before the Bing.

The present variety of cherry tree is still further characterized by the stem of the fruit being easily detached from the fruiting spurs yet firmly attached to the fruit, and there being resistance to the occurrence of spurs and doubling in the fruit in very hot climatic conditions.

The present variety of cherry tree is additionally characterized by fruit having a tough skin, and which advantageously provides substantial resistance to disease and insect penetration, and a lessening of harvest damage.

BRIEF DESCRIPTION OF THE DRAWING

The drawing is an illustration, by photographic reproduction in color, of a limb with leaves and red, hard-ripe fruit; the limb being shown with a portion of the primary scaffold of the tree.

DESCRIPTION OF THE VARIETY

The botanical details of the present new and distinct variety of cherry tree—with color definitions in common color terms—are as follows:

TREE

Size: Large.
Vigor: Vigorous.
Branching habit: Upright.
Density: Dense.
Form: Vase-formed.
Hardiness: Hardy.
Production: Very productive.
Bearing: Regular bearer.

TRUNK

Form: Medium.
Texture: Medium.

BRANCHES

Form: Medium.
Texture: Medium.
Color: Gray. Dull.
Lenticels:
*Number.*—Numerous.
*Size.*—Medium.

LEAVES

Size: Large.
*Average length.*—6″.
*Average width.*—$2\frac{5}{8}$″.
Form: Ovate. Abruptly pointed. Acute tip and base.
Thickness: Medium.
Texture: Smooth.
Color: Dark green.
Margin: Crenate. Coarsely serrate.
Petiole: Medium length. Medium thickness.
Glands: Average number — 2. Alternate. Medium size. Reniform. Red. Positioned on petiole approximately 150″ below leaf blade.
Stipules: Present.

FLOWER BUDS

Size: Medium.
Length: Medium.
Form: Free.
Hardiness: Hardy.

FLOWERS

Date of first bloom: March 16th.
Date of full bloom: March 21st. Early. Approximately four days before Bing.
Size: Medium.
Color: White.

FRUIT

Maturity when described: Hard, red ripe — May 16th.
Harvest period:
*Date of first picking.*—May 19th.
*Date of last picking.*—May 26th.
Size: Uniform. Medium.
*Average diameter axially.*—61/64″.
*Average transversely in suture plane.*—$\frac{3}{4}$″.
Form: Uniform. Symmetrical. Oblong. Broadly compressed toward suture.
Suture: An inconspicuous line extending from base, but discontinuous at apex.
Ventral surface: Lipped toward base throughout both sides.
Lips: Equal.
Base: Rounded.
Apex: Rounded to truncate. Depressed.

SKIN

Thickness: Thick — medium.
Texture: Tough.
Tenacity: Free.
Tendency to crack: Slight in wet season.
Color: Dark purple when full ripe.

FLESH

Color: Red.
*Surface of pit cavity.*—Red, with off-white tinge.
Amygdalin: Wanting.
Juice: Abundant.
Texture: Firm. Crisp.
Fibers: Few. Fine.
Ripens: Evenly.
Flavor: Mild.
Aroma: Distinct.
Eating quality: Best.

STONE

Type: Semifree. Adheres to flesh along both dorsal and ventral edges. Free on sides.
Size: Medium.
*Average length.*—7/16″.
*Average breadth.*—$\frac{3}{8}$″.
*Average thickness.*—5/16″.
Form: Oval.
Base: Straight.
Hilum: Narrow.
Apex: Rounded.
Sides: Equal.
Surface: Smooth.
Pits: Oval (similar to almond).
Ventral edge: Without wing toward base.
Dorsal edge: Full.
Color: Light brown.
Tendency to split: Slight in wet season.

USE

Market.

KEEPING QUALITY

Excellent.

RESISTANCE TO INSECTS

Medium.

RESISTANCE TO DISEASES

Good.

SHIPPING QUALITY

Excellent.

The cherry tree and its fruit herein described may vary in slight detail due to climatic and soil conditions under which the variety may be grown; the present description being of the variety as grown in the Central Valley of California.

It is claimed:

1. A new and distinct variety of cherry tree, substantially as illustrated and described, characterized, in particular, by blooming approximately four days before the Bing, and by the regular and very productive bearing of tough-skinned, firm, sweet, excellent quality, semi-freestone fruit which ripens approximately one week before the Bing; the stem of the fruit being easily detached from the fruiting spurs yet firmly attached to the fruit, and there being resistance to occurrence of spurs and doubling in the fruit in very hot climatic conditions.

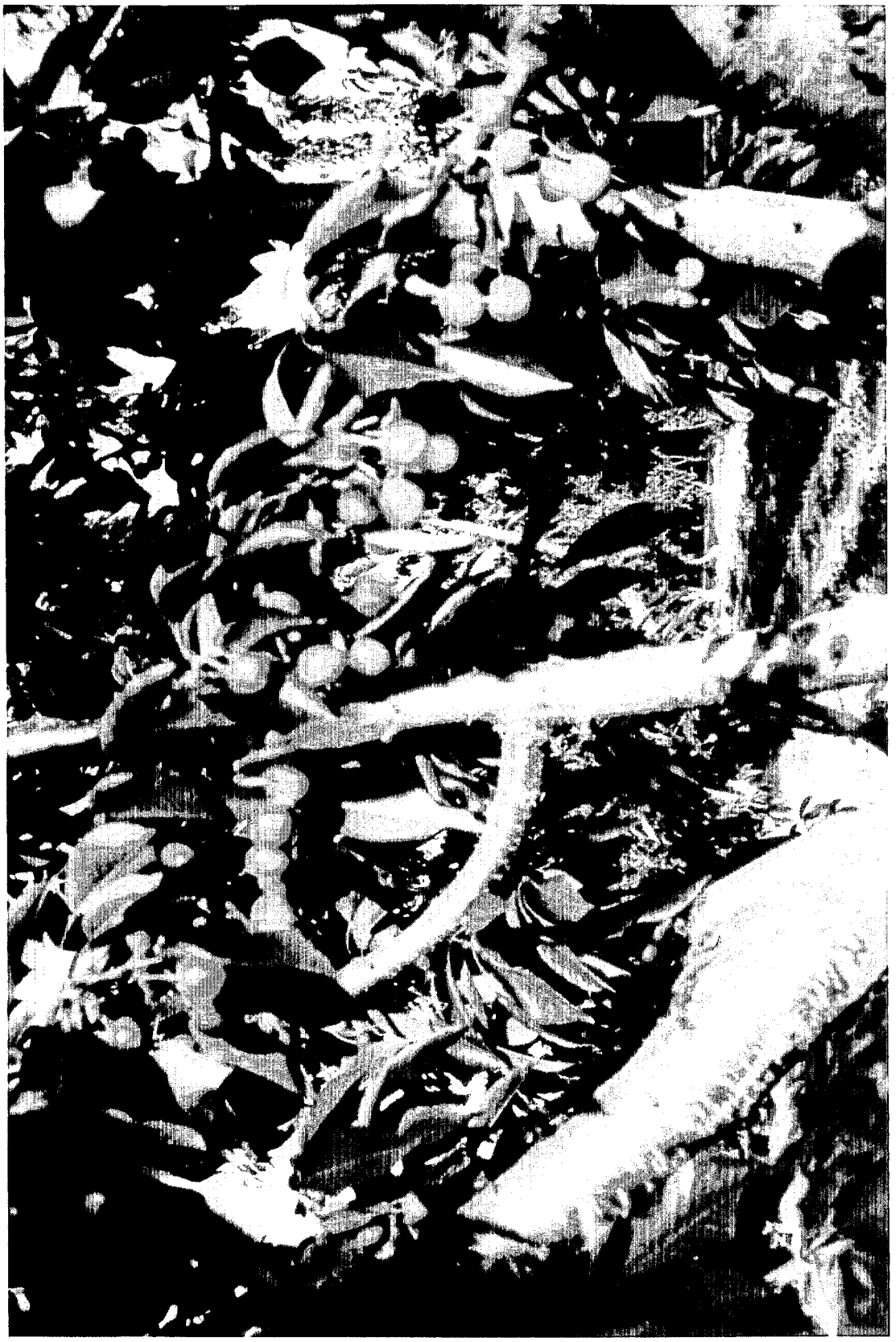

* * * * *